US012629221B2

(12) United States Patent
Weir et al.

(10) Patent No.: US 12,629,221 B2
(45) Date of Patent: May 19, 2026

(54) SYSTEM AND METHOD FOR MINIMALLY INVASIVE CUTTING INSTRUMENT OPERATION

(71) Applicant: INTUITIVE SURGICAL OPERATIONS, INC., Sunnyvale, CA (US)

(72) Inventors: David W. Weir, Menlo Park, CA (US); Michael Waldo, Los Gatos, CA (US); Melody Wu, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 519 days.

(21) Appl. No.: 18/338,599

(22) Filed: Jun. 21, 2023

(65) Prior Publication Data
US 2023/0329812 A1 Oct. 19, 2023

Related U.S. Application Data

(60) Continuation of application No. 17/102,210, filed on Nov. 23, 2020, now Pat. No. 11,737,836, which is a
(Continued)

(51) Int. Cl.
*A61B 34/30* (2016.01)
*A61B 18/14* (2006.01)
(Continued)

(52) U.S. Cl.
CPC .......... *A61B 34/30* (2016.02); *A61B 18/1442* (2013.01); *A61B 18/1445* (2013.01);
(Continued)

(58) Field of Classification Search
CPC ..... A61B 34/30; A61B 34/00; A61B 18/1442; A61B 18/1445; A61B 2090/064;
(Continued)

(56) References Cited

U.S. PATENT DOCUMENTS 9,055,961 B2 6/2015 Manzo et al.
9,089,327 B2 7/2015 Worrell et al.
(Continued)

FOREIGN PATENT DOCUMENTS

CN 102647949 A 8/2012
CN 103442654 A 12/2013
(Continued)

OTHER PUBLICATIONS

European Search Report for Application No. EP16797006, mailed on Dec. 12, 2018, 8 pages.
(Continued)

*Primary Examiner* — Phong Son H Dang
(74) *Attorney, Agent, or Firm* — Artegis Law Group, LLP

(57) ABSTRACT

Techniques for operating an instrument include a computer-assisted device having one or more processors, a motor or other active actuator, and an articulated arm configured to support the instrument having a cutting blade. The one or more processors are configured to control, using the motor or other active actuator, the instrument according to a force or torque limit profile. The force or torque limit profile includes a first force or torque limit used when extending the cutting blade from a first position to a second position, a second force or torque limit used when retracting the cutting blade from the second position to a third position between the first position and the second position and further retracting the cutting blade to the first position, and a third force or torque limit used while the cutting blade is in the first position.

20 Claims, 6 Drawing Sheets

Related U.S. Application Data division of application No. 15/573,096, filed as application No. PCT/US2016/032351 on May 13, 2016, now Pat. No. 10,874,465.

(60) Provisional application No. 62/162,217, filed on May 15, 2015.

(51) Int. Cl.
A61B 34/00 (2016.01)
*A61B 17/00* (2006.01)
*A61B 90/00* (2016.01)

(52) U.S. Cl.
CPC ........ A61B 34/00 (2016.02); *A61B 2017/003* (2013.01); *A61B 2018/1455* (2013.01); *A61B 2090/064* (2016.02); *A61B 2090/066* (2016.02)

(58) Field of Classification Search
CPC ........ A61B 2090/066; A61B 2017/003; A61B 2018/1455
See application file for complete search history.

(56) References Cited

U.S. PATENT DOCUMENTS

| | | | |
|---|---|---|---|
| 9,125,645 | B1 | 9/2015 | Martin et al. |
| 9,173,655 | B2 * | 11/2015 | Martin ............. A61B 17/06133 |
| 9,314,307 | B2 | 4/2016 | Richmond et al. |
| 9,375,212 | B2 | 6/2016 | Martin et al. |
| 9,615,888 | B2 | 4/2017 | Manzo et al. |
| 10,874,465 | B2 | 12/2020 | Weir et al. |
| 2006/0069396 | A1 | 3/2006 | Meade et al. |
| 2006/0282089 | A1 | 12/2006 | Stokes et al. |
| 2010/0152751 | A1 | 6/2010 | Meade et al. |
| 2010/0274244 | A1 | 10/2010 | Heard |
| 2011/0087220 | A1 | 4/2011 | Felder et al. |
| 2012/0215220 | A1 * | 8/2012 | Manzo ................... A61B 34/71 606/46 |
| 2012/0283727 | A1 | 11/2012 | Twomey |
| 2012/0310221 | A1 | 12/2012 | Durant et al. |
| 2012/0310254 | A1 * | 12/2012 | Manzo ................. A61B 17/072 606/130 |
| 2012/0310256 | A1 | 12/2012 | Brisson |
| 2013/0030428 | A1 * | 1/2013 | Worrell ................ A61B 5/0205 606/208 |
| 2014/0005718 | A1 | 1/2014 | Shelton, IV et al. |
| 2014/0172015 | A1 | 6/2014 | Martin et al. |
| 2018/0242967 | A1 | 8/2018 | Meade |
| 2021/0068906 | A1 | 3/2021 | Weir et al. |

FOREIGN PATENT DOCUMENTS

| | | |
|---|---|---|
| CN | 103687564 A | 3/2014 |
| EP | 2243439 A1 | 10/2010 |
| EP | 2248481 B1 | 6/2014 |
| JP | S60132550 A | 7/1985 |
| WO | WO-2010039387 A1 | 4/2010 |
| WO | WO-2011044343 A2 | 4/2011 |
| WO | WO-2012112888 A2 | 8/2012 |
| WO | WO-2012166807 A1 | 12/2012 |
| WO | WO-2012166815 A1 | 12/2012 |
| WO | WO-2014110564 A1 | 7/2014 |

OTHER PUBLICATIONS

International Search Report and Written Opinion for Application No. PCT/US2016/032351, mailed on Aug. 18, 2016, 12 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.
Extended European Search Report for Application No. EP23181552.3, mailed on Sep. 25, 2023, 08 pages.

* cited by examiner

SYSTEM AND METHOD FOR MINIMALLY INVASIVE CUTTING INSTRUMENT OPERATION

RELATED APPLICATIONS

This patent application is a continuation of U.S. patent application Ser. No. 17/102,210 (filed Nov. 23, 2020), which is divisional of U.S. patent application Ser. No. 15/573,096 (filed on Nov. 9, 2017), which is a U.S. National Stage patent application of International Patent Application No. PCT/US2016/032351 (filed on May 13, 2016), the benefit of which is claimed, and claims priority to and the benefit of the filing date of U.S. Provisional Patent Application 62/162,217, entitled "SYSTEM AND METHOD FOR MINIMALLY INVASIVE CUTTING INSTRUMENT OPERATION" and filed May 15, 2015, each of which is incorporated by reference herein in its entirety.

TECHNICAL FIELD

The present disclosure relates generally to operation of devices with articulated arms and end effectors and more particularly to operation of a minimally invasive cutting instrument.

BACKGROUND

More and more devices are being replaced with autonomous and semiautonomous electronic devices. This is especially true in the hospitals of today with large arrays of autonomous and semiautonomous electronic devices being found in operating rooms, interventional suites, intensive care wards, emergency rooms, and the like. For example, glass and mercury thermometers are being replaced with electronic thermometers, intravenous drip lines now include electronic monitors and flow regulators, and traditional hand-held surgical instruments are being replaced by computer-assisted medical devices.

Minimally invasive surgical techniques using computer-assisted medical devices generally attempt to perform surgical and/or other procedures while minimizing damage to healthy tissue. Some minimally invasive procedures may be performed remotely through the use of computer-assisted medical devices with surgical instruments. With many computer-assisted medical devices, a surgeon and/or other medical personnel may typically manipulate input devices using one or more controls on an operator console. As the surgeon and/or other medical personnel operate the various controls at the operator console, the commands are relayed from the operator console to a patient side device to which one or more end effectors and/or surgical instruments are mounted. In this way, the surgeon and/or other medical personnel are able to perform one or more procedures on a patient using the end effectors and/or surgical instruments. Depending upon the desired procedure and/or the surgical instruments in use, the desired procedure may be performed partially or wholly under control of the surgeon and/or medical personnel using teleoperation and/or under semi-autonomous control where the surgical instrument may perform a sequence of operations based on one or more activation actions by the surgeon and/or other medical personnel.

Minimally invasive surgical instruments, whether actuated manually, teleoperatively, and/or semi-autonomously may be used in a variety of operations and/or procedures and may have various configurations. Many such instruments include an end effector mounted at a distal end of a shaft that may be mounted to the distal end of an articulated arm. In many operational scenarios, the shaft may be configured to be inserted (e.g., laparoscopically, thoracoscopically, and/or the like) through an opening (e.g., a body wall incision, a natural orifice, and/or the like) to reach a remote surgical site. In some instruments, an articulating wrist mechanism may be mounted to the distal end of the instrument's shaft to support the end effector with the articulating wrist providing the ability to alter an orientation of the end effector relative to a longitudinal axis of the shaft.

End effectors of different design and/or configuration may be used to perform different tasks, procedures, and functions so as to be allow the surgeon and/or other medical personnel to perform any of a variety of surgical procedures. Examples include, but are not limited to, cauterizing, ablating, suturing, cutting, stapling, fusing, sealing, etc., and/or combinations thereof. Accordingly, end effectors can include a variety of components and/or combinations of components to perform these surgical procedures.

Consistent with the goals of a minimally invasive procedure, the size of the end effector is typically kept as small as possible while still allowing it to perform its intended task. One approach to keeping the size of the end effector small is to accomplish actuation of the end effector through the use of one or more inputs at a proximal end of the surgical instrument, which is typically located externally to the patient. Various gears, levers, pulleys, cables, rods, bands, and/or the like, may then be used to transmit actions from the one or more inputs along the shaft of the surgical instrument and to actuate the end effector. In the case of a computer-assisted medical device with an appropriate surgical instrument, a transmission mechanism at the proximal end of the instrument interfaces with various motors, solenoids, servos, active actuators, hydraulics, pneumatics, and/or the like provided on an articulated arm of the patient side device or a patient side cart. The motors, solenoids, servos, active actuators, hydraulics, pneumatics, and/or the like typically receive control signals through a master controller and provide input in the form of force and/or torque at the proximal end of the transmission mechanism, which the various gears, levers, pulleys, cables, rods, bands, and/or the like ultimately transmit to actuate the end effector at the distal end of the transmission mechanism.

Because of the remote nature of the operation of such end effectors, it may be difficult in some cases for the surgeon and/or other medical personnel to know the position of one or more components of the end effector during actuation to perform a desired procedure. For example, in some cases, other portions of the surgical instrument, including the end effector itself, and/or parts of the anatomy of the patient may hide from view one or more components of the surgical instrument during the actuation of the one or more components. Additionally, when one or more of the components encounters a fault condition while attempting to perform the desired procedure, it may be difficult for the surgeon and/or other medical personnel to detect and/or correct the fault condition due to the limited visibility of the end effector, the limited space in which the surgical instrument operates, the limited access to the surgical instrument, the remote position of the end effector relative to the surgeon and/or other medical personnel, and/or the like.

In addition, safety conditions may also be a factor in the design and/or operation of the surgical instrument. In some examples, the end effector of a surgical tool, such as a cutting tool, may include a sharp cutting blade. When the cutting blade is not actively being used to cut, the cutting blade may be sheathed and/or garaged within a housing on the end effector so that it is generally positioned where it cannot accidentally cut tissue of the patient and/or medical personnel manipulating the surgical tool during non-operation. Similarly, one or more delicate components of the end effector may also be sheathed and/or garaged to prevent damage to the delicate components during non-operation.

Accordingly, improved methods and systems for the operation of surgical instruments, such as a cutting instrument, are desirable. In some examples, it may be desirable to provide automated control of the surgical instrument so as to help ensure that the surgical instrument may be able to successfully perform a desired procedure. In some examples, it may be desirable to provide a configuration of the surgical instrument that supports safety to the patient and/or medical personnel and protection to the surgical instrument during both operation and non-operation.

SUMMARY

Consistent with some embodiments, a surgical cutting instrument for use with a computer-assisted medical device. The surgical cutting instrument includes a drive unit, an end effector located at a distal end of the instrument, a shaft between the drive unit and the end effector, and a garage for housing the cutting blade when the cutting blade is not in use. The end effector includes opposable gripping jaws and a cutting blade. The shaft houses one or more drive mechanisms for coupling force or torque from the drive unit to the end effector. To perform a cutting operation, the instrument is configured to extend the cutting blade from a first position to a second position, retract the cutting blade from the second position to a third position between the first and second positions, and further retract the cutting blade to the first position. While the cutting blade is not in use, the cutting blade is maintained in the first position using a restraining mechanism in the drive unit, force or torque applied by a motor or other active actuator to the drive unit, or both.

Consistent with some embodiments, a method of performing a cutting operation using a surgical cutting instrument for use with a computer-assisted medical device includes holding a cutting blade of an end effector in a first position when the cutting blade is not in use, extending the cutting blade from the first position to a second position by applying force or torque to the drive unit, retracting the cutting blade from the second position to a third position between the first and second positions, and further retracting the cutting blade to the first position. The holding of the cutting blade in the first position is performed by a restraining mechanism of a drive unit, a force or torque applied to the drive unit by a motor or active actuator, or both. The extending and retracting comprise applying force or torque to the drive unit using the motor or active actuator.

Consistent with some embodiments, a non-transitory machine-readable medium includes a plurality of machine-readable instructions which when executed by one or more processors associated with a computer-assisted medical device are adapted to cause the one or more processors to perform a method. The method includes holding a cutting blade of an end effector in a first position when the cutting blade is not in use, extending the cutting blade from the first position to a second position by applying force or torque to the drive unit, retracting the cutting blade from the second position to a third position between the first and second positions, and further retracting the cutting blade to the first position. The holding the cutting blade in the first position is performed by a restraining mechanism of a drive unit, a force or torque applied to the drive unit by a motor or active actuator, or both. The extending and retracting includes applying force or torque to the drive unit using the motor or active actuator.

Consistent with some embodiments, a computer-assisted medical device includes one or more processors, an articulated arm, a motor or other active actuator, and a surgical instrument coupled to a distal end of the articulated arm. The surgical instrument includes a drive unit located at a proximal end of the surgical instrument, an end effector located at a distal end of the surgical instrument, a shaft between the drive unit and the end effector, and a garage for housing the cutting blade when the cutting blade is not in use. The end effector comprising opposable gripping jaws and a cutting blade. The shaft houses one or more drive mechanisms for coupling force or torque from the drive unit to the end effector. The computer-assisted medical device is configured to perform a cutting operation using the cutting blade by extending the cutting blade from a first position to a second position, retracting the cutting blade from the second position to a third position between the first and second positions, and further retracting the cutting blade to the first position. While the cutting blade is not in use, the cutting blade is maintained in the first position using a restraining mechanism in the drive unit, force or torque applied by the motor or other active actuator to the drive unit, or both.

In the figures, elements having the same designations have the same or similar functions.

DETAILED DESCRIPTION

In the following description, specific details are set forth describing some embodiments consistent with the present disclosure. It will be apparent to one skilled in the art, however, that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

Figure 1:
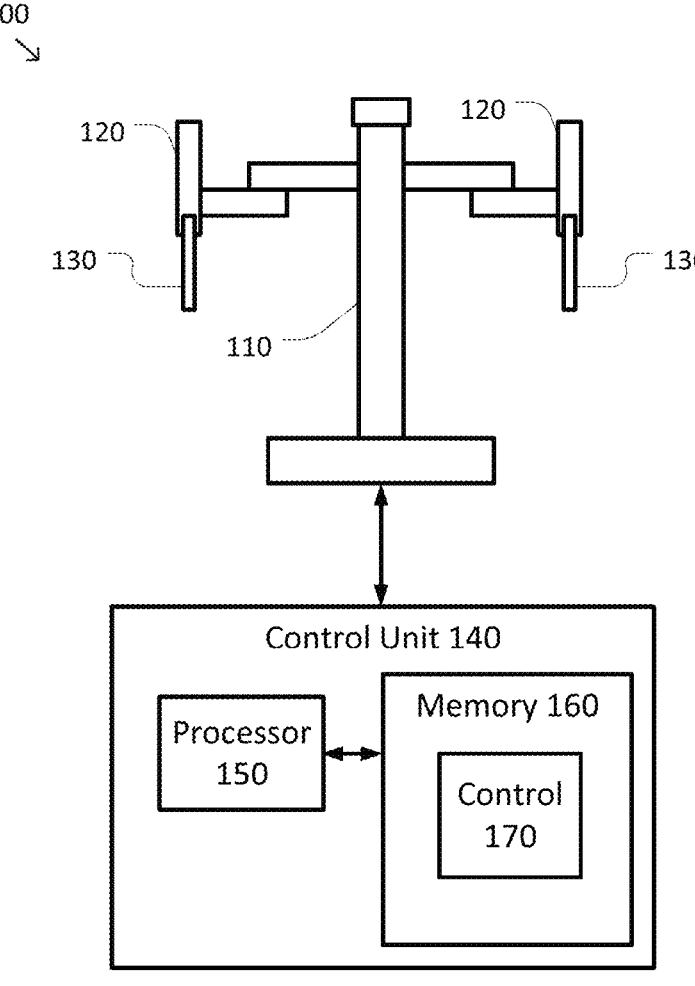
FIG. 1 is a simplified diagram of a computer-assisted system according to some embodiments.

FIG. 1 is a simplified diagram of a computer-assisted system 100 according to some embodiments. As shown in FIG. 1, computer-assisted system 100 includes a computer-assisted device 110 with one or more movable or articulated arms 120. Each of the one or more articulated arms 120 may support one or more instruments 130. In some examples, computer-assisted device 110 may be consistent with a computer-assisted surgical device. The one or more articulated arms 120 may each provide support for medical instruments 130 such as surgical instruments, imaging devices, and/or the like. In some examples, the instruments 130 may include end effectors that are capable of, but are not limited to, performing, gripping, retracting, cauterizing, ablating, suturing, cutting, stapling, fusing, sealing, etc., and/or combinations thereof.

Computer-assisted device 110 may further be coupled to an operator workstation (not shown), which may include one or more master controls for operating the computer-assisted device 110, the one or more articulated arms 120, and/or the instruments 130. In some examples, the one or more master controls may include master manipulators, levers, pedals, switches, keys, knobs, triggers, and/or the like. In some embodiments, computer-assisted device 110 and the operator workstation may correspond to a da Vinci® Surgical System commercialized by Intuitive Surgical, Inc. of Sunnyvale, California. In some embodiments, computer-assisted surgical devices with other configurations, fewer or more articulated arms, and/or the like may be used with computer-assisted system 100.

Computer-assisted device 110 is coupled to a control unit 140 via an interface. The interface may include one or more cables, fibers, connectors, and/or buses and may further include one or more networks with one or more network switching and/or routing devices. Control unit 140 includes a processor 150 coupled to memory 160. Operation of control unit 140 is controlled by processor 150. And although control unit 140 is shown with only one processor 150, it is understood that processor 150 may be representative of one or more central processing units, multi-core processors, microprocessors, microcontrollers, digital signal processors, field programmable gate arrays (FPGAs), application specific integrated circuits (ASICs), and/or the like in control unit 140. Control unit 140 may be implemented as a stand-alone subsystem and/or board added to a computing device or as a virtual machine. In some embodiments, control unit 140 may be included as part of the operator workstation and/or operated separately from, but in coordination with the operator workstation.

Memory 160 may be used to store software executed by control unit 140 and/or one or more data structures used during operation of control unit 140. Memory 160 may include one or more types of machine readable media. Some common forms of machine readable media may include floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

As shown in FIG. 1, memory 160 includes a control application 170 that may be used to support autonomous, semiautonomous, and/or teleoperated control of computer-assisted device 110. Control application 170 may include one or more application programming interfaces (APIs) for receiving position, motion, force, torque, and/or other sensor information from computer-assisted device 110, articulated arms 120, and/or instruments 130, exchanging position, motion, force, torque, and/or collision avoidance information with other control units regarding other devices, and/or planning and/or assisting in the planning of motion for computer-assisted device 110, articulated arms 120, and/or instruments 130. In some examples, control application 170 may further support autonomous, semiautonomous, and/or teleoperated control of the instruments 130 during a surgical procedure. And although control application 170 is depicted as a software application, control application 170 may be implemented using hardware, software, and/or a combination of hardware and software.

In some embodiments, computer-assisted system 100 may be found in an operating room and/or an interventional suite. And although computer-assisted system 100 includes only one computer-assisted device 110 with two articulated arms 120 and corresponding instruments 130, one of ordinary skill would understand that computer-assisted system 100 may include any number of computer-assisted devices with articulated arms and/or instruments of similar and/or different in design from computer-assisted device 110. In some examples, each of the computer-assisted devices may include fewer or more articulated arms and/or instruments.

Figures 2, 3:
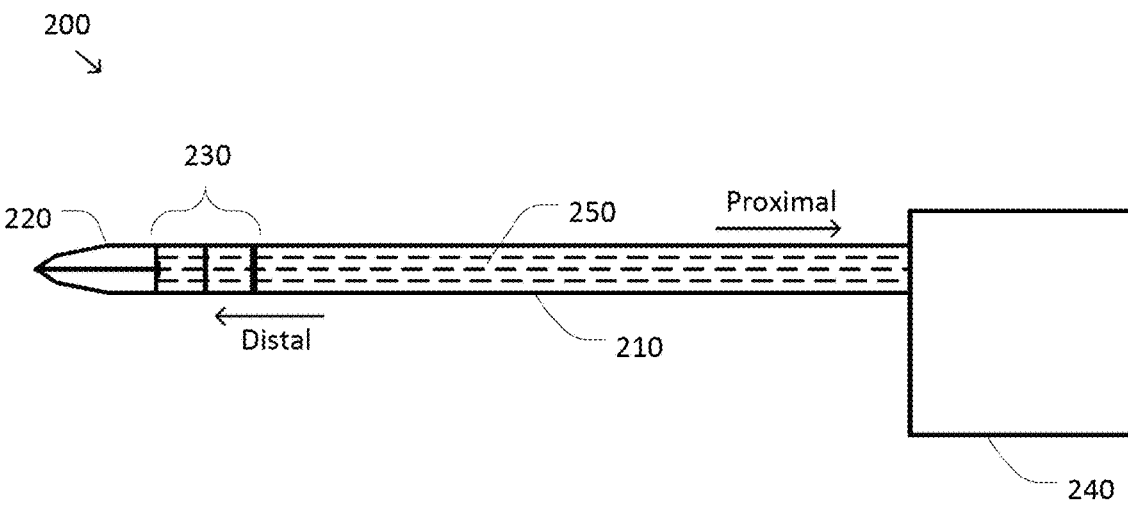
FIG. 2 is a simplified diagram showing a minimally invasive surgical instrument according to some embodiments.
FIG. 3 is a simplified perspective diagram of the distal end of the surgical instrument of FIG. 2 according to some embodiments.

FIG. 2 is a simplified diagram showing a minimally invasive surgical instrument 200 according to some embodiments. In some embodiments, surgical instrument 200 may be consistent with any of the instruments 130 of FIG. 1. The directions "proximal" and "distal" as depicted in FIG. 2 and as used herein help describe the relative orientation and location of components of surgical instrument 200. Distal generally refers to elements in a direction further along a kinematic chain from a base of a computer-assisted device, such as computer-assisted device 110, and/or or closest to the surgical work site in the intended operational use of the surgical instrument 200. Proximal generally refers to elements in a direction closer along a kinematic chain toward the base of the computer-assisted device and/or one of the articulated arms of the computer-assisted device.

As shown in FIG. 2, surgical instrument 200 includes a long shaft 210 used to couple an end effector 220 located at a distal end of shaft 210 to where the surgical instrument 200 is mounted to an articulated arm and/or a computer-assisted device at a proximal end of shaft 210. Depending upon the particular procedure for which the surgical instrument 200 is being used, shaft 210 may be inserted through an opening (e.g., a body wall incision, a natural orifice, and/or the like) in order to place end effector 220 in proximity to a remote surgical site located within the anatomy of a patient. As further shown in FIG. 2, end effector 220 is generally consistent with a two-jawed gripper-style end effector, which in some embodiments may further include a cutting and/or a fusing or sealing mechanism as is described in further detail below with respect to FIGS. 3 and 4A-4C. However, one of ordinary skill would understand that different surgical instruments 200 with different end effectors 220 are possible and may be consistent with the embodiments of surgical instrument 200 as described elsewhere herein.

A surgical instrument, such as surgical instrument 200 with end effector 220 typically relies on multiple degrees of freedom (DOFs) during its operation. Depending upon the configuration of surgical instrument 200 and the articulated arm and/or computer-assisted device to which it is mounted, various DOFs that may be used to position, orient, and/or operate end effector 220 are possible. In some examples, shaft 210 may be inserted in a distal direction and/or retreated in a proximal direction to provide an insertion DOF that may be used to control how deep within the anatomy of the patient that end effector 220 is placed. In some examples, shaft 210 may be able rotate about its longitudinal axis to provide a roll DOF that may be used to rotate end effector 220. In some examples, additional flexibility in the position and/or orientation of end effector 220 may be provided by an articulated wrist 230 that is used to couple end effector 220 to the distal end of shaft 210. In some examples, articulated wrist 230 may include one or more rotational joints, such as one or more roll, pitch or yaw joints that may provide one or more "roll," "pitch," and "yaw" DOF(s), respectively, that may be used to control an orientation of end effector 220 relative to the longitudinal axis of shaft 210. In some examples, the one or more rotational joints may include a pitch and a yaw joint; a roll, a pitch, and a yaw joint, a roll, a pitch, and a roll joint; and/or the like. In some examples, end effector 220 may further include a grip DOF used to control the opening and closing of the jaws of end effector 220 and/or an activation DOF used to control the extension, retraction, and/or operation of a cutting mechanism as is described in further detail below.

Surgical instrument 200 further includes a drive system 240 located at the proximal end of shaft 210. Drive system 240 includes one or more components for introducing forces and/or torques to surgical instrument 200 that may be used to manipulate the various DOFs supported by surgical instrument 200. In some examples, drive system 240 may include one or more motors, solenoids, servos, active actuators, hydraulic actuators, pneumatic actuators, and/or the like that are operated based on signals received from a control unit, such as control unit 140 of FIG. 1. In some examples, the signals may include one or more currents, voltages, pulse-width modulated wave forms, and/or the like. In some examples, drive system 240 may include one or more shafts, gears, pulleys, rods, bands, and/or the like which may be coupled to corresponding motors, solenoids, servos, active actuators, hydraulics, pneumatics, and/or the like that are part of the articulated arm, such as any of the articulated arms 120, to which surgical instrument 200 is mounted. In some examples, the one or more drive inputs, such as shafts, gears, pulleys, rods, bands, and/or the like, may be used to receive forces and/or torques from the motors, solenoids, servos, active actuators, hydraulics, pneumatics, and/or the like and apply those forces and/or torques to adjust the various DOFs of surgical instrument 200.

In some embodiments, the forces and/or torques generated by and/or received by drive system 240 may be transferred from drive system 240 and along shaft 210 to the various joints and/or elements of surgical instrument 200 located distal to drive system 240 using one or more drive mechanisms 250. In some examples, the one or more drive mechanisms 250 may include one or more gears, levers, pulleys, cables, rods, bands, and/or the like. In some examples, shaft 210 is hollow and the drive mechanisms 250 pass along the inside of shaft 210 from drive system 240 to the corresponding DOF in end effector 220 and/or articulated wrist 230. In some examples, each of the drive mechanisms 250 may be a cable disposed inside a hollow sheath or lumen in a Bowden cable like configuration. In some examples, the cable and/or the inside of the lumen may be coated with a low-friction coating such as polytetrafluoroethylene (PTFE) and/or the like. In some examples, as the proximal end of each of the cables is pulled and/or pushed inside drive system 240, such as by wrapping and/or unwrapping the cable about a capstan or shaft, the distal end of the cable moves accordingly and applies a suitable force and/or torque to adjust one of the DOFs of end effector 220, articulated wrist 230, and/or surgical instrument 200.

FIG. 3 is a simplified perspective diagram of the distal end of surgical instrument 200 according to some embodiments. As shown in FIG. 3, the distal end of surgical instrument 200 is depicted so as to show additional details of end effector 220, articulated wrist 230, and drive mechanisms 250. In more detail, end effector 220 includes opposing jaws 310 shown in an open position. Jaws 310 are configured to move between open and closed positions so that end effector 220 may be used during a procedure to grip and release tissue and/or other structures, such as sutures, located at the surgical site. In some examples, jaws 310 may be operated together as a single unit with both jaws 310 opening and/or closing at the same time. In some examples, jaws 310 may be opened and/or closed independently so that, for example, one jaw 310 could be held steady which the other jaw 310 may be opened and/or closed.

Figure 4A:
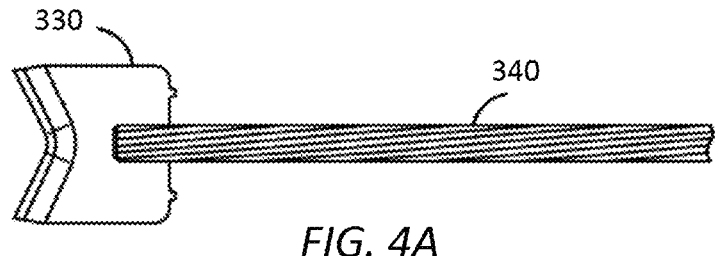
FIGS. 4A-4C are simplified cut-away diagrams of the end effector of FIGS. 2 and 3 according to some embodiments.
Figure 4B:
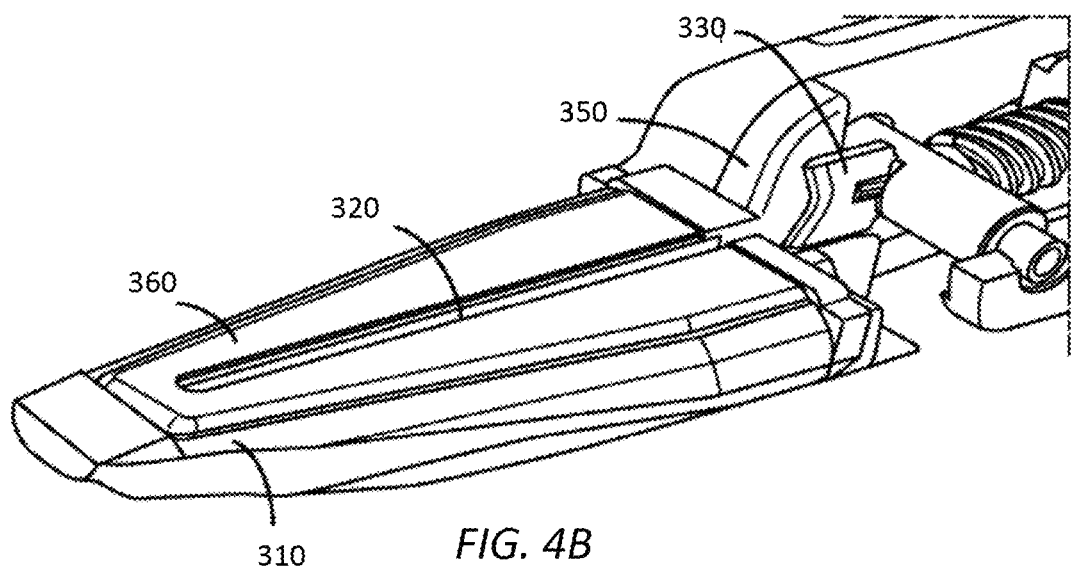
Figure 4C:
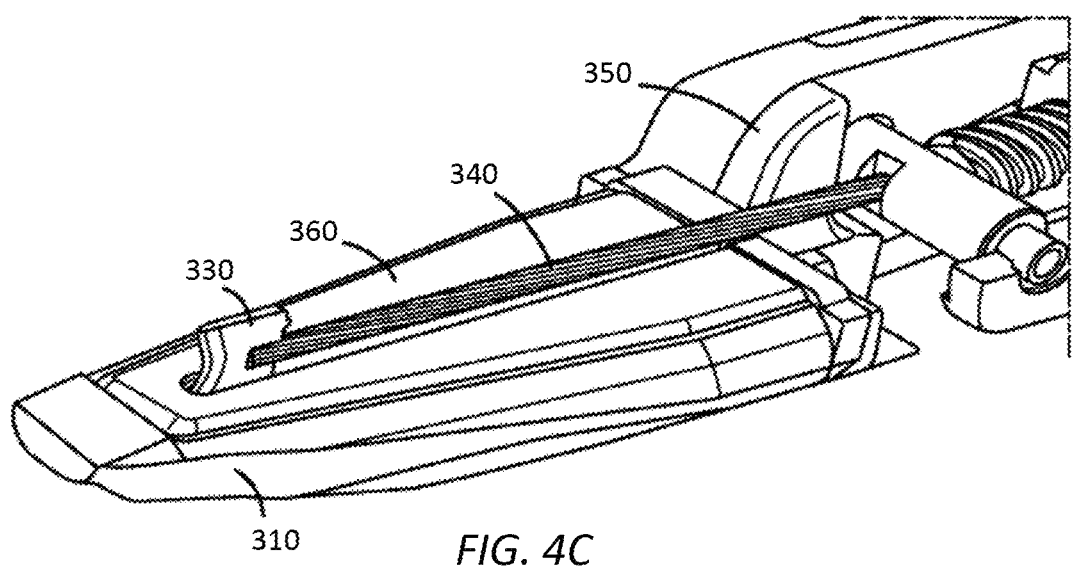

FIG. 3 shows that a gripping surface on an inside of each of jaws 310 includes a corresponding groove 320, which may act as a guide for a cutting blade 330, although the groove 320 may be omitted from one or more of jaws 310. As cutting blade 330 is extended toward the distal end of end effector 220 and/or retracted toward the proximal end of end effector 220, each of the grooves 320 may aid in the alignment and/or positioning of cutting blade 330 during a cutting operation. Extraction and/or retraction of cutting blade 330 is accomplished using a drive component 340 to which cutting blade 330 is attached. In some examples, drive component 340 pushes on cutting blade 330 to extend cutting blade 330 and pulls on cutting blade 330 to retract cutting blade 330. Use and positioning of cutting blade 330 is shown in FIGS. 4A-4C, which are simplified cut-away diagrams of end effector 220 according to some embodiments. FIG. 4A shows the relationship between cutting blade 330 and drive component 340.

End effector 220 further includes a garage feature 350 located at a proximal end of jaws 310. Garage feature 350 includes an opening through which both drive component 340 and cutting blade 330 may pass. Garage feature 350 is configured to provide a safe storage area for cutting blade 330 when cutting blade 330 is not in use. Thus, when cutting blade 330 is not actively being used as part of a cutting operation, end effector 220 is configured so that cutting blade 330 may be retracted into garage feature 350 in a "garaged" or stored position in which cutting blade 330 is recessed proximally behind jaws 310 as shown in FIG. 4B. Cutting blade 330 may additionally be extended to a position in which cutting blade 330 is positioned at or near a distal end of one of the grooves 320 as shown in FIG. 4C. In some examples, the positioning of cutting blade 330 as shown in FIG. 4C may correspond to a position of cutting blade 330 during a cutting operation.

In some examples, end effector 220 and surgical instrument 200 are designed so that the default or home position of cutting blade 330 is within garage feature 350. This arrangement of garage feature 350 may provide several features to end effector 220. In some examples, when cutting blade 330 is retracted into garage feature 350, the sharp cutting edge of cutting blade 330 is effectively sheathed so that cutting blade 330 is unlikely to accidentally cut tissue during a procedure and/or medical personnel handling surgical instrument 200 and/or end effector 220 before and/or after a procedure. In some examples, when cutting blade 330 is retracted into garage feature 350, cutting blade 330 may also be protected from damage, such as accidental dulling, when cutting blade 330 is not actively being used to cut.

Referring back to FIG. 3, in some embodiments, the gripping surface on the inside of each of jaws 310 may further include one or more optional electrodes 360. In some examples, electrodes 360 may be used to deliver electrosurgical energy to fuse tissue being held between jaws 310. In some examples, electrodes 360 may provide an electrocautery, fusing, and/or sealing feature to end effector 220 so that tissue may be cut and/or fused/sealed using the same surgical tool 200.

In some embodiments, operation of jaws 310, cutting blade 330, and/or the joints of articulated wrist 230 may be accomplished using corresponding ones of the drive mechanisms 250. In some examples, when jaws 310 are operated independently, a distal end of two of the drive mechanisms 250 (one for each of jaws 310) may be coupled to a respective jaw 310 so that as the corresponding drive mechanism 250 applies a pull and/or a pushing force (for example, using a cable, lead screw, and/or the like), the respective jaw 310 may be opened and/or closed. In some examples, when jaws 310 are operated together, both jaws 310 may be coupled to the distal end of the same drive mechanism 250. In some examples, drive component 340 may be coupled to a distal end of a corresponding drive mechanism 250 so that forces and/or torques applied to the corresponding drive mechanism 250 may be transferred to the push and/or pull motion of drive component 340. In some examples, additional drive mechanisms 350 may be used to operate the roll, pitch, and/or yaw DOFs in articulated wrist 230.

Figure 5:
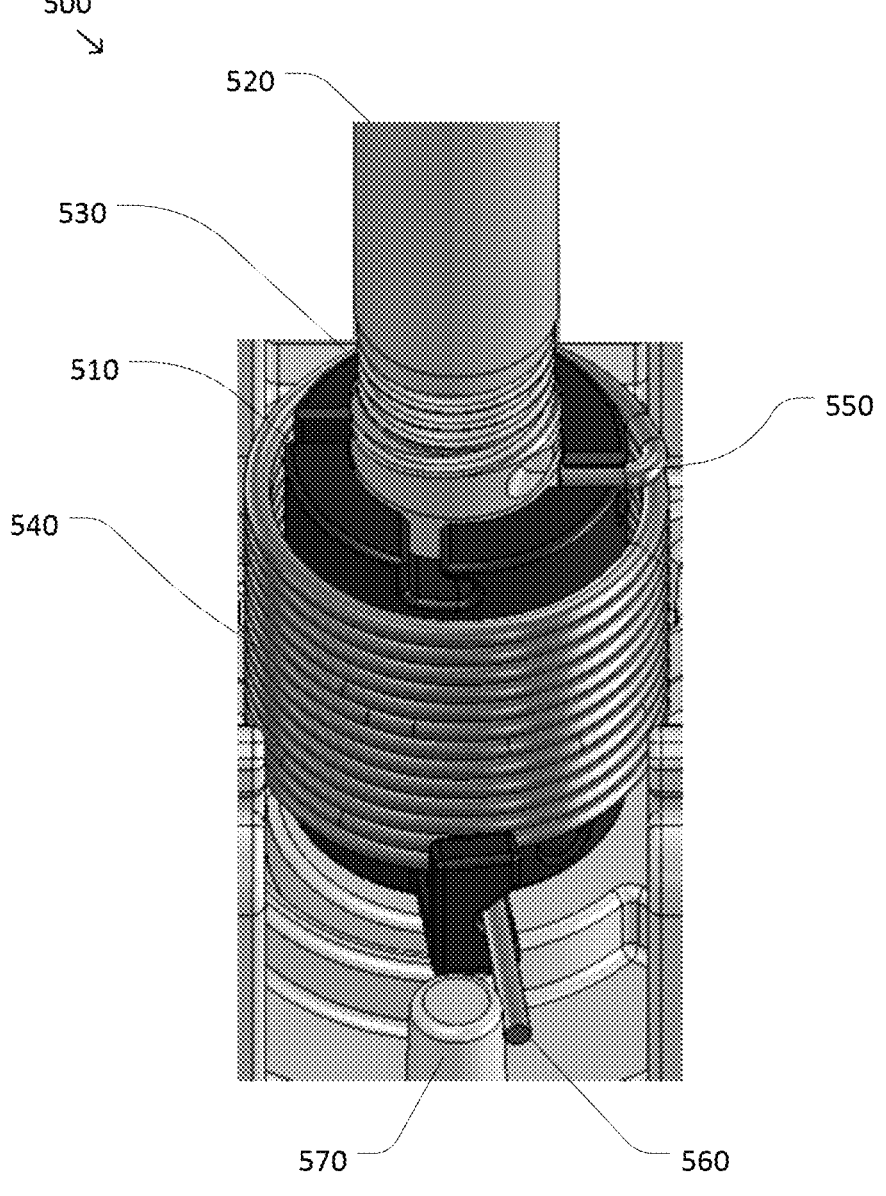
FIG. 5 is a simplified perspective diagram of a drive unit for a degree of freedom according to some embodiments.

FIG. 5 is a simplified perspective diagram of a drive unit 500 for a degree of freedom according to some embodiments. According to some embodiments, drive unit 500 may be representative of a portion of the components in drive system 240 of FIG. 2. As shown in FIG. 5, drive unit 500 is based on a rotational actuation approach in which a capstan 510 is rotated to actuate a DOF. Capstan 510 is coupled to a drive shaft 520 which may be the drive shaft of a motor, servo, active actuator, hydraulic actuator, pneumatic actuator, and/or the like (not shown). As torque is applied to drive shaft 520 and drive shaft 520 and capstan 510 are rotated, a cable 530 attached to capstan 510 and/or drive shaft 520 may be further wrapped around and/or unwrapped from around capstan 510 and/or drive shaft 520. When cable 530 is attached to the proximal end of a corresponding drive mechanism, such as any of drive mechanisms 250, the wrapping and unwrapping of the cable may translate into corresponding pulling and pushing forces and/or torques that may be applied to a DOF of an end effector located at the distal end of the drive mechanism. In some examples, rotation of capstan 510 and drive shaft 520 and the corresponding wrapping and/or unwrapping of cable 530 may result in opening and/or closing of gripper jaws such as jaws 310, extending and/or retracting of a cutting blade such as cutting blade 330, flexing and/or unflexing of articulated wrist joints, and/or the like. In some examples, monitoring a rotation angle and/or rotational velocity of capstan 510 and/or drive shaft 520 may also provide an indication of a current position and/or velocity of the corresponding DOF coupled to cable 530 through the corresponding drive mechanism. Thus, when drive unit 500 is used in conjunction with the DOFs of surgical instrument 200, the rotation angle and/or rotational velocity of capstan 510 and/or drive shaft 520 may provide useful feedback on the angle to which jaws 310 are opened, the position of cutting blade 330, and/or the pitch and/or yaw angle of articulated wrist 230 depending on which of the drive mechanisms 250 cable 530 is coupled.

Because it is often desirable for a DOF in an end effector to be configured with a default, rest, and/or home position when the DOF is not being actuated, in some embodiments a drive unit, such as drive unit 500 may include some type of resistive and/or restraining mechanism to return drive unit 500 to a corresponding home position. In some examples, use of a home position for a DOF may support configuration of a surgical instrument, such as surgical instrument 200, where gripping jaws are automatically closed and/or mostly closed, cutting blades are retracted into a garage feature, articulated wrist joints are straightened, and/or the like. As shown in FIG. 5, drive unit 500 includes a restraining mechanism in the form of a torsion spring 540. Torsion spring 540 is shown attached at one end 550 to capstan 510 and wrapped around capstan 510. As capstan 510 is rotated, a second end 560 of torsion spring 540 may freely rotate until it rotates up against a stop 570 that may be part of a body of drive unit 500. As capstan 510 continues to rotate after the second end 560 of torsion spring 540 is against stop 570, torsion spring 540 will begin to provide a restraining and/or return to home force and/or torque to capstan 510 as dictated by the amount of rotation of capstan 510 and a spring constant of torsion spring 540. Thus, as greater amounts of rotation are applied to capstan 510, torsion spring 540 applies increasing return to home force and/or torque to capstan 510. It is this return to home force and/or torque on capstan 510 that may be used, for example, to close the gripping jaws, retract the cutting blade, and/or straighten the articulated wrist joints.

Although FIG. 5 shows the restraining mechanism as a torsion spring wrapped around capstan 510, one of ordinary skill would recognize other possible restraining mechanisms and/or configurations for the restraining mechanisms to accomplish a similar restraining/return to home function. In some examples, the body of drive unit 500 may further include a second stop to provide a return to home force and/or torque to capstan 510 in an opposite direction to the return to home force and/or torque resulting from stop 570. In some examples, the second end 560 of torsion spring 540 may be mounted to the body of drive unit 500 so that no free movement of torsion spring 540 is permitted before torsion spring 540 begins applying return to home force and/or torque to capstan 510 and/or torsion spring 540 applies at least some return to home force and/or torque to capstan 510 even without rotation of capstan 510.

According to some embodiments, selection of an appropriately sized restraining mechanism, such as the spring constant for torsion spring 540, for a DOF of an end effector may present several challenges to the designer of a surgical instrument. In some situations it may be desirable to select the size of the restraining mechanism to overcome any likely and/or reasonable interference with the desired return to home function of the corresponding drive unit of the DOF. In some examples, selection of the size of the restraining mechanism to overcome any likely and/or reasonable interference tends to oversize the restraining mechanism for many of the possible operational scenarios. Additionally, as the size of the restraining mechanism increases, a corresponding greater force or torque has to be applied to the drive unit to overcome the restraining mechanism. In some examples, this may include the use of a larger motor, solenoid, servo, active actuator, hydraulic actuator, pneumatic actuator, and/or the like to overcome the restraining mechanism or result in a smaller operational margin for the DOF that results in less force and/or torque being available to drive the DOF to perform an operation. For example, less cutting force and/or torque may be available to apply to a cutting blade to perform a cut. In some examples, this larger return to home force and/or torque may increase the stress and/or strain placed on the drive mechanism that may result in increased wear on the drive mechanism, stretching of the drive mechanism, and/or the like. In some examples, the stretching of the drive mechanism may result in the drive mechanism and the corresponding DOF becoming out of tolerance, thus resulting is a diminished ability to control the DOF as desired. In some examples, this larger return to home force and/or torque may increase the likelihood of injury to a patient and/or medical personnel, such as when a return to home gripping force may result in damage and/or tearing of tissue still located between the gripping jaws of an end effector.

One possible compromise is to size the restraining mechanism to provide sufficient return to home force and/or torque to return the DOF to the home position when the surgical instrument is not being used (i.e., when the surgical instrument is not mounted to a corresponding articulated arm and/or computer-assisted device) and to use the motor, solenoid, servo, active actuator, hydraulic actuator, pneumatic actuator, and/or the like coupled to the drive unit to provide additional return to home force and/or torque during operational scenarios where additional return to home force and/or torque is desired. Under this compromise, it is generally possible to use smaller motors, solenoids, servos, active actuators, hydraulic actuators, pneumatic actuators, and/or the like while still providing a desired amount of operational margin to support the desired operations of the corresponding surgical instrument. In some examples, the restraining mechanism may be sized to provide approximately 0 N to 10 N of return to home force and/or a similar torque to the DOF.

Figure 6:
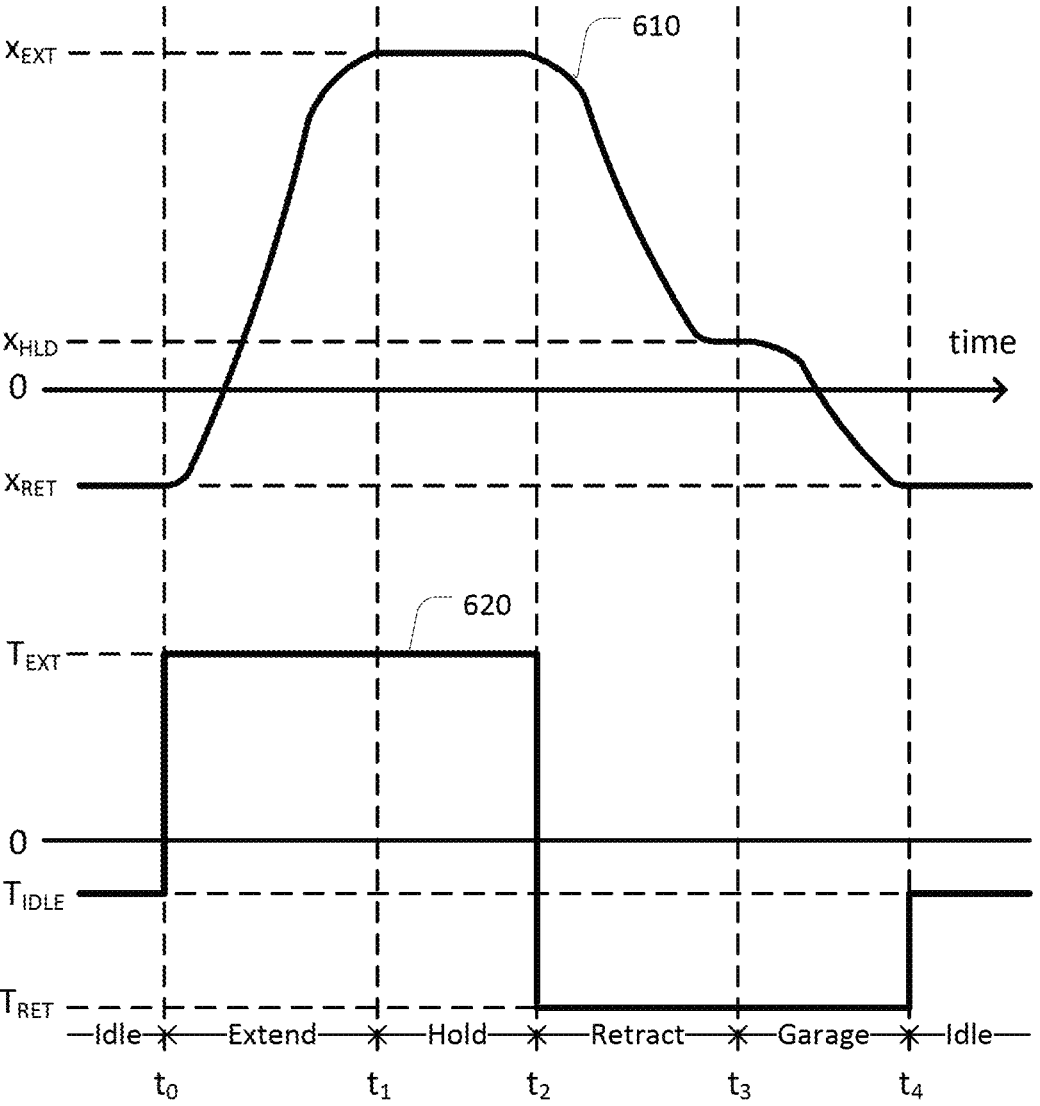
FIG. 6 is a simplified diagram of a positional profile and a corresponding torque limit profile for a cutting operation according to some embodiments.

FIG. 6 is a simplified diagram of a positional profile 610 and a corresponding torque limit profile 620 for a cutting operation according to some embodiments. In some embodiments, positional profile 610 and torque limit profile 620 may be suitable for application to cutting blade 330 using drive unit 500. As shown in FIG. 6, positional profile 610 and torque limit profile 620 include a four-phase cutting operation beginning at a time to. The four phases include an extending phase from $t_0$ to $t_1$, a holding phase from $t_1$ to $t_2$, a retracting phase from $t_2$ to $t_3$, and a garaging phase from $t_3$ to $t_4$. For the purposes of discussing FIG. 6, the position of the cutting blade will be described relative to an x position of the cutting blade with more positive positions being in a distal direction, however, one of ordinary skill would understand that the positions for the cutting blade may be represented using any suitable positional and/or rotational axis such as a position along an axis defined by groove 320, a rotational angle of capstan 510, and/or the like and/or could alternatively be characterized with positive values in a more proximal direction.

One of the goals of the extending phase is to rapidly extend the cutting blade from a retracted position of $x_{RET}$ to an extended position of $x_{EXT}$. In some examples, $x_{RET}$ may correspond to a garaged and/or home position of the cutting blade. In some examples, the zero position for the cutting blade may correspond to an outer or distal edge of a garage feature, such as garage feature 350, when the articulated wrist is in a straight or unflexed position. In some examples, $x_{RET}$ is selected as a sufficiently negative value, such as approximately −3 mm, to account for variability among different drive mechanisms and/or drive units. In some examples, a negative $x_{RET}$ may also address possible deviations in the drive mechanism caused by the flexing of the articulated wrist in the surgical instrument. In some examples, as the articulated wrist flexes, the drive mechanism may be subject to bending and/or movement within the hollow shaft (e.g., shaft 210) of the surgical instrument. As the drive mechanism bends and/or moves an effective distance, as seen by the drive mechanism, may change between the distal end at the cutting blade and the proximal end at the drive unit. As a result, the amount of retraction to return the cutting blade to the garage may vary between situations where the articulated wrist is flexed and unflexed. In some examples, $x_{EXT}$ may correspond to a fully and/or mostly extended position for the cutting blade, such as approximately +18 mm, so that the cutting blade does not strike the end of a guiding groove, such as one of the grooves 320, and/or to reduce the likelihood of cutting blade exposure where the cutting blade comes out of the guiding grooves and is not able to be retracted back into the garaged or home position. In some examples, a duration of the extending phase (i.e., the time between $t_0$ and $t_1$) may be rather rapid and may vary, for example, from 50 ms to 250 ms in length, and preferably 175 ms in length.

One of the goals of the holding phase is to continue to command the cutting blade to full extension at $x_{EXT}$ to account for operational scenarios when it takes longer than the duration of the extending phase for the cutting blade to transition from $x_{RET}$ to $x_{EXT}$. In some examples, the holding phase may also reduce the likelihood that the cutting blade will be retracted before it has reached the desired extension. In some examples, a duration of the holding phase (i.e., the time between $t_1$ and $t_2$) may be similar in magnitude to the duration of the extending phase or slightly shorter and may vary, for example, from 50 ms to 150 ms in length, and preferably 100 ms in length.

Retraction of the cutting blade may occur using a two-phase operation that includes the retracting phase and the garaging phase. One of the goals of the retracting phase is to rapidly retract the cutting blade to a position $x_{HLD}$ that corresponds to retracting the cutting blade to a hold position that is most of the way back to the garaged or home position, such as approximately +1 mm. Following the retracting phase, the cutting blade is more completely retracted to the $x_{RET}$ position during the garaging phase. In some examples, the use of the two-phase operation of retracting followed by garaging may reduce the likelihood that the cutting blade may rebound back out the garage during retraction relative to a single-phase operation directly to $x_{RET}$ and/or reduce the magnitude of loads applied to the cutting blade and drive mechanism during the garaging phase. In some examples, a duration of the retracting phase (i.e., the time between $t_2$ and $t_3$) may vary, for example, from 50 ms to 175 ms in length, and preferably 120 ms in length. In some examples, a duration of the garaging phase (i.e., the time between $t_3$ and $t_4$) may vary, for example, from 75 ms to 200 ms in length, and preferably 150 ms in length.

In some examples, the time periods before to, when the cutting operation begins, and after $t_4$, when the cutting operation ends, may correspond to idle phases where the cutting blade is held at the garaged or home position of $x_{RET}$ using force and/or torque provided by both the restraining mechanism of the drive unit and the motor, solenoid, servo, active actuator, hydraulic actuator, pneumatic actuator, and/or the like used to operate the drive unit as is discussed further below.

According to some embodiments, the positional profile 610 of FIG. 6 represents a desired position of the cutting blade during a cutting operation. In some examples, positional profile 610 may be converted to a time sequence of position commands for the cutting blade and the motor, solenoid, server actuator, hydraulic actuator, pneumatic actuator, and/or the like used to actuate the drive unit for the cutting blade. In some examples, interpolation and/or curve fitting using, for example, a cubic spline may be used to determine the time sequence of position commands so as to provide a smooth positional profile 610 or position trajectory for the cutting blade throughout the cutting operation. In some examples, the actual position of the cutting blade and/or the drive unit may be monitored during the cutting operation using one or more sensors to determine whether the cutting blade and/or the drive unit are able to follow the positional profile 610. In some examples, when the cutting blade and/or the drive unit are not able to follow the positional profile 610 within a predefined tolerance, an audio, visual, and/or textual alert may be provided to the surgeon and/or other medical personnel to indicate that the cutting operation may not have been successful. In some examples, the cutting operation may not be successful when the cutting blade is not able to extend to $x_{EXT}$ and/or becomes exposed and cannot return to $x_{RET}$.

According to some embodiments, even though the cutting blade is generally operated using a position control approach as indicated by positional profile 610, the control unit for the motor, solenoid, servo, active actuator, hydraulic actuator, pneumatic actuator, and/or the like driving the drive unit for the cutting blade may be subject to upper and/or lower force and/or torque limits. In some examples, the force and/or torque limits may be determined based on the size of the motor, solenoid, servo, active actuator, hydraulic actuator, pneumatic actuator, and/or the like, to reduce the likelihood of damage and/or excessive wear to the drive unit, drive mechanism, and/or cutting blade, to reduce power used to actuate the cutting blade, and/or to address the practical needs of the cutting operation. Torque limit profile 620 represents one possible such profile and, although torque limit profile 620 is described in terms of torques, other control actuators and/or control systems may alternatively use limits to voltage, current, force, duty cycle, and/or the like as would be understood by one of ordinary skill in the art.

As shown in FIG. 6, torque limit profile 620 uses a combination of three torque limits depending upon which phase of the cutting operation the cutting blade is in and/or whether the cutting blade is currently idle. And although the torque limits are characterized with a positive torque limit value corresponding to an extending direction, one of ordinary skill would understand that the sign of the torque limit is arbitrary depending on the configuration of the control actuators and/or the drive unit for the cutting blade. In torque limit profile 620, a torque limit of TEXT is used during the extending and holding phases of the cutting operation. In some examples, TEXT is set at a sufficiently high limit to overcome any restraining mechanism, such as torsion spring 540, in the drive unit and to supply suitable actuating force and/or torque to allow the cutting blade to cut tissue while the cutting blade is being extended. In some examples, TEXT may be in a range suitable for the cutting blade to deliver 15 N to 20 N of cutting force during extension.

A torque limit of $T_{RET}$ is used during the retracting and garaging phases. In some examples, $T_{RET}$ is set at a sufficiently high limit to overcome any tissue and/or other debris from the cutting operation that may interfere with the desired retraction and/or garaging of the cutting blade after cutting has taken place. In some examples, $T_{RET}$ may have approximately the same magnitude as TEXT, but with an opposite sign so that $T_{RET}$ may be in a range suitable for delivering 15 N to 20 N of retracting force to the cutting blade. In some examples, $T_{RET}$ may have a magnitude smaller than that of TEXT to account for the torque used to overcome the restraining mechanism during extension and to reflect the assistance provided by the restraining mechanism during retraction.

A torque limit of $T_{IDLE}$ is used when the cutting blade is idle. In some examples, $T_{IDLE}$ is set to a lower magnitude than $T_{RET}$, but with a magnitude sufficient to assist the restraining mechanism in keeping the cutting blade garaged during periods of non-use. In some examples, the magnitude of TIME may be set to avoid placing excessive strain on the motor, solenoid, servo, active actuator, hydraulic actuator, pneumatic actuator, drive mechanism, drive, unit, etc. due to attempts to retract the cutting blade beyond any physical limits imposed by the end effector and/or garage feature due to the negative retraction position of $x_{RET}$. In some examples, $T_{IDLE}$ may be in a range suitable for delivering 0 N to 5 N of retracting force to the cutting blade.

As discussed above and further emphasized here, FIG. 6 is merely an example which should not unduly limit the scope of the claims. One of ordinary skill in the art would recognize many variations, alternatives, and modifications. According to some embodiments, different positional and/or torque limit profiles are possible depending upon the desired operation of a particular DOF, such as the cutting DOF more directly discussed in FIG. 6. In some examples, different torque limit values may be used in the extending and holding phases and/or in the retracting and garaging phases. In some examples, a more complex torque limit profile using ramps and/or the like are possible. In some examples, the torque limit may be variable based on the current position of the cutting blade.

Figure 7:
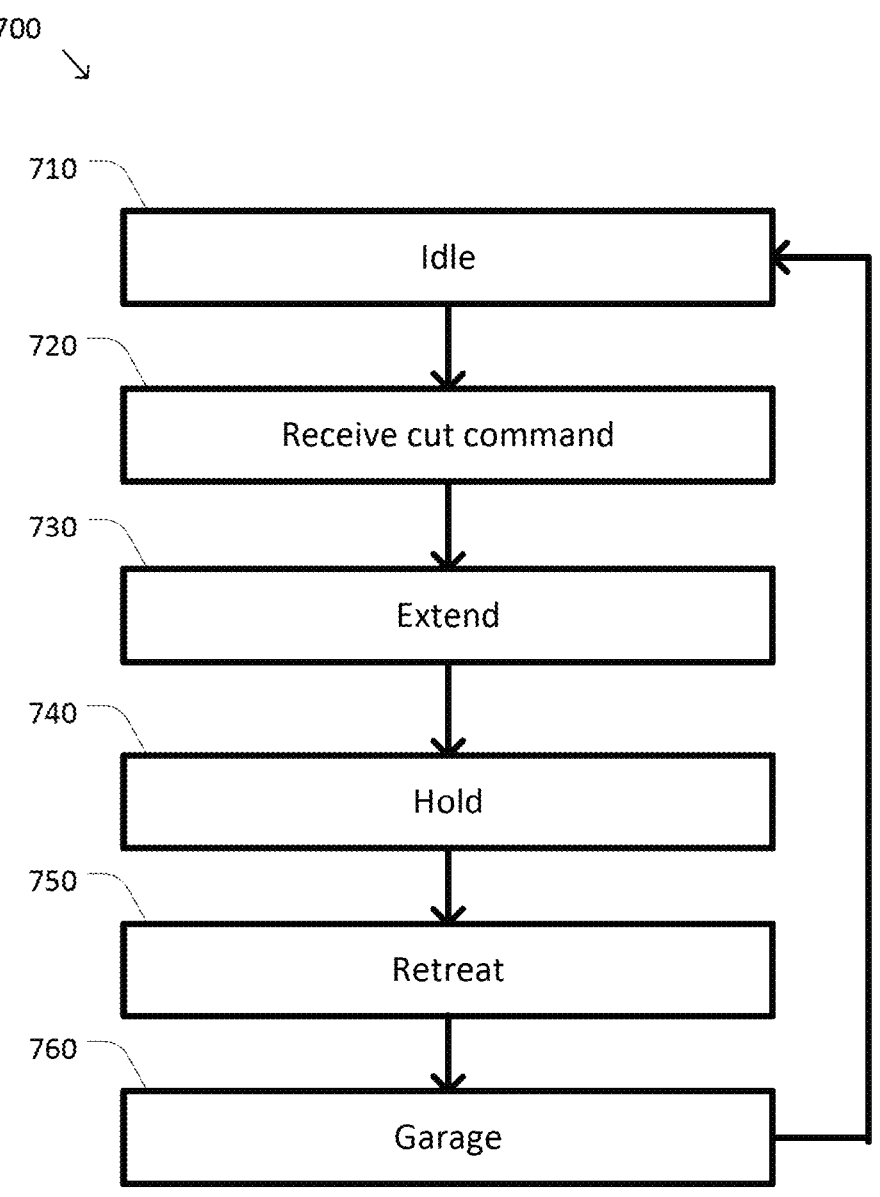
FIG. 7 is a simplified diagram of a method for performing a cutting operation according to some embodiments.

FIG. 7 is a simplified diagram of a method 700 for performing a cutting operation according to some embodiments. One or more of the processes 710-760 of method 700 may be implemented, at least in part, in the form of executable code stored on non-transient, tangible, machine readable media that when run by one or more processors (e.g., the processor 150 in control unit 140) may cause the one or more processors to perform one or more of the processes 710-760. In some embodiments, method 700 may be performed by an application, such as control application 170. In some embodiments, method 700 may be used to extend and retract a cutting blade, such as cutting blade 330, of a surgical instrument, such as surgical instrument 200. In some embodiments, the cutting operation of method 700 may be performed according to positional profile 610 and/or torque limit profile 620. In some embodiments, drive components such as those described in FIGS. 2, 3, and 4A-4C may be used during the performance of method 700 to extend, retract, and/or maintain the cutting blade in an idle position.

At a process 710, a cutting blade is maintained in an idle position. In some examples, the idle position may correspond to a garaged and/or home position where the cutting blade is protected from damage and/or the cutting blade is sheathed within a garage feature, such as garage feature 350, so as to reduce the likelihood of accidentally cutting tissue and/or medical personnel when active cutting is not taking place. In some examples, the idle position may correspond to a slightly negative position, such as the position $x_{RET}$ of positional profile 610. In some examples, the cutting blade may be held in the idle position based on force and/or torque applied to the cutting blade by a drive component, a drive mechanism, a drive unit, and/or an actuator such as a motor, solenoid, servo, active actuator, hydraulic actuator, pneumatic actuator, and/or the like. In some examples, the applied force and/or torque may be applied using a restraining mechanism, such as torsion spring 540, the actuator, and/or both. In some examples, the amount of force and/or torque applied by the actuator may be subject to a limit, such as $T_{IDLE}$ from torque limit profile 620. In some examples, as long as the cutting blade is not being used for cutting the cutting blade may be maintained in the idle position. In some examples, process 710 may correspond to the periods labeled as idle periods in FIG. 6.

At a process 720, a cut command is received. In some examples, a surgeon and/or other personnel may request that a cutting operation take place. In some examples, the cutting operation may be requested using one or more master controls, such as one or more master manipulators, levers, pedals, switches, keys, knobs, triggers, and/or the like located on an operator console. In some examples, the requested cutting operation may be received by a control application, such as control application 170, via an interrupt, an input polling operation, an API call, and/or the like.

At a process 730, the cutting blade is extended. In some examples, a first phase of the cutting operation may include actuating the cutting blade to rapidly extend from the idle position of process to 710 to an extended position, such as the position $x_{EXT}$ of positional profile 610. In some examples, the actuation of the cutting blade during process 730 may include providing a time sequence of position commands to the drive unit operating the DOF associated with the cutting blade so that a smooth positional profile, such as positional profile 610 during the extending phase, is commanded for the cutting blade. In some examples, the cutting blade may be extended based on force and/or torque applied to the cutting blade by a drive component, a drive mechanism, a drive unit, and/or an actuator such as a motor, solenoid, servo, active actuator, hydraulic actuator, pneumatic actuator, and/or the like. In some examples, the amount of force and/or torque applied to the cutting blade may be selected so as to overcome any restraining mechanism used to keep the cutting blade in the idle position as well as to deliver sufficient cutting force to cut tissue. In some examples, the amount of force and/or torque applied may be subject to a limit, such as TEXT from torque limit profile 620. In some examples, process 730 may correspond to the period labeled as the extending period in FIG. 6.

At a process 740, the cutting blade is held in the extended position. In some examples, a second phase of the cutting operation may include continuing to actuate the cutting blade to extend to the extended position of process 730. In some examples, this extended position may correspond to the position $x_{EXT}$ of positional profile 610. In some examples, the cutting blade may continue to be extended and/or held at the extended position based on force and/or torque applied to the cutting blade by a drive component, a drive mechanism, a drive unit, and/or an actuator such as a motor, solenoid, servo, active actuator, hydraulic actuator, pneumatic actuator, and/or the like. In some examples, the amount of force and/or torque applied to the cutting blade may be selected so as to overcome any restraining mechanism used to keep the cutting blade in the idle position as well as to deliver sufficient cutting force to cut tissue. In some examples, the amount of force and/or torque applied may be subject to a limit, such as TEXT from torque limit profile 620. In some examples, process 740 may correspond to the period labeled as the hold period in FIG. 6.

At a process 750, the cutting blade is retracted. In some examples, a third phase of the cutting operation may include actuating the cutting blade to rapidly retract from the extended position of processes 730 and/or 740 to a hold position, such as the position $x_{HLD}$ of positional profile 610, located most of the way back toward the idle position of process 710. In some examples, the actuation of the cutting blade during process 750 may include providing a time sequence of position commands to the drive unit operating the DOF associated with the cutting blade so that a smooth positional profile, such as positional profile 610 during the retracting phase, is commanded for the cutting blade. In some examples, the cutting blade may be retracted based on force and/or torque applied to the cutting blade by a drive component, a drive mechanism, a drive unit, and/or an actuator such as a motor, solenoid, servo, active actuator, hydraulic actuator, pneumatic actuator, and/or the like. In some examples, the amount of force and/or torque applied to the cutting blade may be selected so as to overcome any likely tissue, debris, and/or the like that may be interfering with retraction of the cutting blade. In some examples, the retracting may additionally be aided by a restraining mechanism used to keep the cutting blade in the idle position. In some examples, the amount of force and/or torque applied may be subject to a limit, such as $T_{RET}$ from torque limit profile 620. In some examples, process 750 may correspond to the period labeled as the retracting period in FIG. 6.

At a process 760, the cutting blade is garaged. In some examples, a fourth phase of the cutting operation may include actuating the cutting blade to retract from the hold position of process 750 to the idle position of process 710. In some examples, the actuation of the cutting blade during process 760 may include providing a time sequence of position commands to the drive unit operating the DOF associated with the cutting blade so that a smooth positional profile, such as positional profile 610 during the garaging phase, is commanded for the cutting blade. In some examples, the cutting blade may be retracted based on force and/or torque applied to the cutting blade by a drive component, a drive mechanism, a drive unit, and/or an actuator such as a motor, solenoid, servo, active actuator, hydraulic actuator, pneumatic actuator, and/or the like. In some examples, the amount of force and/or torque applied to the cutting blade may be selected so as to overcome any likely tissue, debris, and/or the like that may be interfering with garaging of the cutting blade. In some examples, the garaging may additionally be aided by a restraining mechanism used to keep the cutting blade in the idle position. In some examples, the amount of force and/or torque applied may be subject to a limit, such as $T_{RET}$ from torque limit profile 620. In some examples, process 760 may correspond to the period labeled as the garaging period in FIG. 6.

After the cutting blade is garaged during process 760, the cutting operation is complete and the cutting blade is maintained in the idle position using process 710 until another cutting command is received.

Although not shown in FIG. 7, one of ordinary skill would understand that method 700 may be performed in cooperation with one or more monitoring and/or reporting processes. In some examples, the actual position of the cutting blade and/or the drive unit for the cutting blade may be monitored using one or more sensors during method 700 to determine whether the cutting blade and/or the drive unit are able to follow the positional profile for the cutting blade, such as the positional profile 610. In some examples, when the cutting blade and/or the drive unit are not able to follow the positional profile within a predefined tolerance, an audio, visual, and/or textual alert may be provided to the surgeon and/or other medical personnel to indicate that the cutting operation may not have been successful. In some examples, the cutting operation may not be successful when the cutting blade is not able to extend as commanded during processes 730 and/or 740. In some examples, the cutting operation may not be successful when the cutting blade becomes exposed and cannot return to the garage. In some examples, a warning and/or an alert using one or more audio, visual, and/or textual alerts may be issued when any of the extracting, holding, retracting, and/or garaging operations reach one of the force and/or torque limits corresponding to the respective cutting operation phase.

Some examples of control units, such as control unit 140 may include non-transient, tangible, machine readable media that include executable code that when run by one or more processors (e.g., processor 150) may cause the one or more processors to perform the processes of method 700. Some common forms of machine readable media that may include the processes of method 700 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A computer-assisted device comprising:
   one or more processors;
   a motor or other active actuator; and
   an articulated arm configured to support an instrument having a cutting blade;
   wherein the one or more processors are configured to control, using the motor or other active actuator, the instrument according to a force or torque limit profile;
   wherein the force or torque limit profile comprises:
      a first force or torque limit used when extending the cutting blade from a first position to a second position;
      a second force or torque limit used when retracting the cutting blade from the second position to a third position between the first position and the second position and further retracting the cutting blade to the first position; and
      a third force or torque limit used while the cutting blade is in the first position.

2. The computer-assisted device of claim 1, wherein one or more of gripping jaws of the instrument include a groove to assist in guiding the cutting blade during the extending and retracting.

3. The computer-assisted device of claim 1, wherein the first position is within a garage of the instrument.

4. The computer-assisted device of claim 1, wherein the third position corresponds to a position where the cutting blade is retracted to just outside a garage of the instrument.

5. The computer-assisted device of claim 1, wherein the one or more processors are further configured to control, using the motor or other active actuator, the cutting blade to follow a positional profile subject to the first, second, and third force or torque limits, the positional profile comprising a time sequence of desired positions describing a smooth trajectory for the cutting blade between the first, second, and third positions.

6. The computer-assisted device of claim 5, wherein the positional profile comprises a holding phase for holding the cutting blade in the second position before retracting the cutting blade to the third position.

7. The computer-assisted device of claim 5, wherein the positional profile comprises a phase for holding the cutting blade in the third position before further retracting the cutting blade to the first position.

8. The computer-assisted device of claim 1, wherein a magnitude of the first force or torque limit and a magnitude of the second force or torque limit is a same force or torque limit magnitude.

9. The computer-assisted device of claim 1, wherein a magnitude of the first force or torque limit is greater than a magnitude of the second force or torque limit.

10. The computer-assisted device of claim 1, wherein a magnitude of the third force or torque limit is lower than a magnitude of the second force or torque limit.

11. The computer-assisted device of claim 1, wherein a difference between a magnitude of the first force or torque limit and a magnitude of the second force or torque limit is based on a force or torque applied by a restraining mechanism used to help maintain the cutting blade in the first position.

12. A method of operating a cutting instrument, the method comprising:
   controlling, by a control unit using a motor or other active actuator, a drive unit of an instrument according to a force or torque limit profile, wherein the force or torque limit profile comprises:
      a first force or torque limit used when extending a cutting blade of the instrument from a first position to a second position;
      a second force or torque limit used when retracting the cutting blade from the second position to a third position between the first position and the second position and further retracting the cutting blade to the first position; and
      a third force or torque limit used while the cutting blade is in the first position.

13. The method of claim 12, wherein the first position is within a garage.

14. The method of claim 12, wherein the third position corresponds to a position where the cutting blade is retracted to just outside a garage.

15. The method of claim 12, further comprising controlling, by the control unit using the motor or other active actuator, the cutting blade to follow a positional profile subject to the first, second, and third force or torque limits, the positional profile comprising a time sequence of desired positions describing a smooth trajectory for the cutting blade between the first, second, and third positions.

16. The method of claim 12, wherein a difference between a magnitude of the first force or torque limit and a magnitude of the second force or torque limit is based on a force or torque applied by a restraining mechanism used to help maintain the cutting blade in the first position.

17. A non-transitory machine-readable medium comprising a plurality of machine-readable instructions which when executed by one or more processors associated with a computer-assisted device are adapted to cause the one or more processors to perform a method comprising:

controlling, using a motor or other active actuator, a drive unit of an instrument according to a force or torque limit profile, wherein the force or torque limit profile comprises:

a first force or torque limit used when extending a cutting blade of the instrument from a first position to a second position;

a second force or torque limit used when retracting the cutting blade from the second position to a third position between the first position and the second position and further retracting the cutting blade to the first position; and a third force or torque limit used while the cutting blade is in the first position.

18. The non-transitory machine-readable medium of claim 17, wherein:

the first position is within a garage; and the third position corresponds to a position where the cutting blade is retracted to just outside the garage.

19. The non-transitory machine-readable medium of claim 17, wherein the method further comprises controlling, using the motor or other active actuator, the cutting blade to follow a positional profile subject to the first, second, and third force or torque limits, the positional profile comprising a time sequence of desired positions describing a smooth trajectory for the cutting blade between the first, second, and third positions.

20. The non-transitory machine-readable medium of claim 17, wherein a difference between a magnitude of the first force or torque limit and a magnitude of the second force or torque limit is based on a force or torque applied by a restraining mechanism used to help maintain the cutting blade in the first position.

\* \* \* \* \*